(12) United States Patent
Shields

(10) Patent No.: US 11,439,428 B2
(45) Date of Patent: Sep. 13, 2022

(54) HYBRID GUIDE

(71) Applicant: Samuel S. Shields, Reno, NV (US)

(72) Inventor: Sam Shields, Reno, NV (US)

( * ) Notice: Subject to any disclaimer, the term of this patent is extended or adjusted under 35 U.S.C. 154(b) by 566 days.

(21) Appl. No.: 16/326,483

(22) PCT Filed: Aug. 14, 2017

(86) PCT No.: PCT/US2017/046832
§ 371 (c)(1),
(2) Date: Feb. 19, 2019

(87) PCT Pub. No.: WO2018/035068
PCT Pub. Date: Feb. 22, 2018

(65) Prior Publication Data
US 2021/0282805 A1    Sep. 16, 2021

Related U.S. Application Data

(60) Provisional application No. 62/376,805, filed on Aug. 18, 2016.

(51) Int. Cl.
*A61B 17/34* (2006.01)
*A61B 8/00* (2006.01)

(52) U.S. Cl.
CPC ........ *A61B 17/3403* (2013.01); *A61B 8/4209* (2013.01); *A61B 2017/3407* (2013.01); *A61B 2017/3413* (2013.01)

(58) Field of Classification Search
CPC .............. A61B 17/3403; A61B 8/4209; A61B 2017/3413; A61B 2017/3407; A61B 8/0841
See application file for complete search history.

(56) References Cited

U.S. PATENT DOCUMENTS

| | | | |
|---|---|---|---|
| 10,314,559 B2* | 6/2019 | Razzaque | A61B 8/0841 |
| 11,191,928 B2* | 12/2021 | Almansouri | A61M 25/0662 |
| 2009/0143684 A1* | 6/2009 | Cermak | A61B 8/4422 |
| | | | 600/461 |
| 2010/0041990 A1* | 2/2010 | Schlitt | A61B 17/3403 |
| | | | 600/439 |

(Continued)

FOREIGN PATENT DOCUMENTS

WO    WO-2015159129 A1 *  10/2015  ............. A61B 34/20

*Primary Examiner* — Bill Thomson
*Assistant Examiner* — Zainab Mohammed Aldarraji
(74) *Attorney, Agent, or Firm* — Jonathan D. Feuchtwang (57) ABSTRACT

A positioning fixture for use with an ultrasound transducer comprising a base having a planar bottom surface and top surface, each having two long edges and two short edges, the top surface facing away from the bottom surface; first and second echogenic targeting bands recessed below the bottom surface of the housing; a pair of long sidewalls provided on and extending orthogonally from the top surface, one long sidewall of the pair of long sidewalls attached to each of the two long edges; a guide release on the top surface, attached to one of the two short edges on the top surface; a long axis needle guide on the top surface, attached to another of the two short edges; and a receptacle cooperatively defined by the pair of long sidewalls, the guide release and the long axis needle guide, the receptacle sized to accommodate the ultrasound transducer.

9 Claims, 10 Drawing Sheets

(56) References Cited

U.S. PATENT DOCUMENTS

| | | | | |
|---|---|---|---|---|
| 2013/0150714 A1* | 6/2013 | Howlett | ............... | A61B 8/4483 |
| | | | | 600/439 |
| 2014/0200445 A1* | 7/2014 | Boezaart | .............. | A61B 8/4455 |
| | | | | 600/424 |
| 2014/0343404 A1* | 11/2014 | Razzaque | ............ | A61B 8/0841 |
| | | | | 600/424 |
| 2015/0289929 A1* | 10/2015 | Toth | ..................... | A61B 5/6858 |
| | | | | 600/372 |
| 2016/0117857 A1* | 4/2016 | State | ..................... | A61B 34/20 |
| | | | | 345/420 |
| 2016/0338724 A1* | 11/2016 | Sinelnikov | ............... | A61B 8/12 |
| 2017/0035385 A1* | 2/2017 | Sasady | .................. | A61B 34/20 |
| 2017/0128042 A1* | 5/2017 | Desai | .................. | A61B 8/4281 |

\* cited by examiner

HYBRID GUIDE

CROSS-REFERENCE TO RELATED APPLICATIONS

This application claims priority to and the benefit of PCT Application PCT/US2017/046832 (WO 2017/035068) filed Aug. 14, 2017 which claims priority from U.S. Provisional Patent Application No. 62/376,805 entitled "HYBRID GUIDE" filed Aug. 18, 2016.

BRIEF DESCRIPTION

The invention relates to needle guides used for inserting intravenous needles under ultrasound visualization.

BACKGROUND

Traditional intravenous access has been obtained by palpation and visualization of the vein or artery to be cannulated. This method is transitioning to ultrasound-guided intravascular catheterization. Ultrasound guidance has been shown to be safer and more reliable, thus benefiting the patient.

There are two techniques for using ultrasound for vascular cannulation. These two methods are the short axis approach, also known as "out of plane" approach. The second method is the long axis approach which is also known as the "in plane" approach. Each of these approaches has its advantages and disadvantages.

The benefit of the short axis approach is the ability to distinguish structures such as nerve bundles, veins, and arteries. Also, short axis allows the clinician to center the needle over the vessel prior to needle insertion into the skin. In addition, by moving the ultrasound transducer beam along the long axis of the vessel the clinician confirms linearity of the vessel. The disadvantage of the short axis approach is the lack of visualization of the entirety of the needle shaft during the procedure. The clinician only sees the portion of the needle penetrating the ultrasound beam. The needle, therefore, can puncture through the posterior wall of the vessel going deeper than anticipated into the patient without the knowledge of the clinician.

The benefit of the long axis approach is the ability to visualize the shaft of the needle in the entirety of the procedure. If done appropriately, the clinician can confirm entrance into the vessel without penetrating the posterior wall and injuring deeper structures. The disadvantage to the long axis approach is the difficulty in keeping the needle shaft in the thin 1 mm ultrasound beam during the entirety of the procedure.

A recommended approach is a hybrid of the two. The clinician first locates the vessel in the short axis. Then the ultrasound probe is pressed into the flesh to confirm collapse of the vein distinguishing it from the artery. After this is done, the ultrasound probe is moved up and down the long axis of the vein to confirm linearity of the vessel. Once this is confirmed, the vessel is centered on the ultrasound screen. The clinician aligns the needle in the center of the probe coinciding with the center of the ultrasound screen over the centered vessel. The skin is then punctured. Once the skin is punctured the ultrasound probe is lifted and turned 90° into the long axis. The clinician then identifies both the vein and the needle and arranges them in the long axis of the beam. The needle is then visualized entering the vein, confirming cannulation without posterior wall penetration of the vessel.

The hybrid procedure described, using first the short axis, then the long axis, works well. However, there is some tactile difficulty—particularly, keeping the shaft of the needle in the long axis of the vein continuously within the ultrasound beam during the procedure.

SUMMARY OF THE INVENTION

Disclosed is a positioning fixture for use with an ultrasound transducer comprising a housing having a planar, generally rectangular bottom surface having two parallel long edges and two parallel short edges; a pair of long sidewalls, one said long sidewall attached to each of said two parallel long edges; a guide release attached to one of said two parallel short edges; a long axis needle guide attached to another of said two parallel short edges; and a receptacle cooperatively defined by said pair of long sidewalls, said quick release and said needle insertion guide, said receptacle sized to accommodate the ultrasound transducer.

The positioning fixture of the above-described embodiment further comprising a short axis notch provided on at least one of the two long sidewalls, said notch sized and configured to accept a needle.

The positioning fixture of the above-described embodiment further comprising a short axis notch provided on at least one of the two long sidewalls, said short axis notch sized and configured to accept a needle.

The positioning fixture of the above-described embodiment wherein the long axis needle guide includes a long axis notch sized and configured to accept a needle.

The positioning fixture of the above-described embodiment including any of the aforementioned improvements further comprising first and second echogenic targeting bands provided on the bottom surface of the housing.

The positioning fixture of the above-described embodiment including any of the aforementioned improvements further comprising two or more support fins provided within a base of the receptacle, said support fins configured to support and grip the transducer.

The positioning fixture of the above-described embodiment including any of the aforementioned improvements wherein an angular orientation the long axis needle guide is adjustable.

The positioning fixture of the above-described embodiment including any of the aforementioned improvements wherein the long axis needle guide includes at least two long axis notches provided at different angular orientations.

The positioning fixture of the above-described embodiment including any of the aforementioned improvements wherein the long axis notch defines an angle ranging from 30 to 60 degrees relative to the bottom surface of the housing.

A method of inserting a needle into a patient's vein under ultrasound guidance, comprising:

providing a hybrid guide including: a housing having a planar, generally rectangular bottom surface having two parallel long edges and two parallel short edges; a pair of long sidewalls, one said long sidewall attached to each of said two parallel long edges; a short axis notch provided on at least one of the two long sidewalls, said short axis notch sized and configured to accept a needle; a guide release attached to one of said two parallel short edges; a long axis needle guide attached to another of said two parallel short edges, said long axis needle guide having a long axis notch; and a receptacle cooperatively defined by said pair of long sidewalls, said quick release and said needle insertion guide, said receptacle sized to accommodate the ultrasound transducer;

insert an ultrasound transducer into the receptacle;

adjust a position of the housing under ultrasound visualization such that the short axis notch is centered over the vein;

insert the needle into the short axis notch and pierce the subject's skin;

disengage the needle from the short axis notch by lifting the Hybrid Guide off of the needle, rotate the Hybrid Guide 90 degrees, and place the needle into engagement with the long axis needle guide; and advance the needle into the vein.

DETAILED DESCRIPTION OF THE INVENTION

Sierra Medical Designs has created a unique device to assist the clinician when using the hybrid technique to obtain quick, consistent, accurate and safe vascular access. This device is called the Hybrid Guide 100. The Hybrid Guide 100 is designed to be a single use sterile device that, therefore, decreases risk of infection. Hybrid Guide 100 is composed of a material which is biocompatible and sterilizable.

The Hybrid Guide 100 snaps onto transducer head 109 of an ultrasound probe and forms a snug fit. There is a unique tensioning clip 101/102 that also functions as a guide release 101/102. This clip 101/102 is on the opposite side from the long axis guide 104. The clip 101/102 is ergonomically designed to not interfere with the practitioner's grip on the transducer 109. Clip 101/102 applies constant pressure to firmly stabilize the Hybrid Guide 100 on the transducer head 109. The clip 101/102 includes an easy release tab for removal.

The Hybrid Guide 100 preferably includes an alignment notch 103 on the long side of the ultrasound probe 108. This alignment notch is termed the "short axis notch" 103, and is designed to facilitate centering the needle 110 on the long side of the ultrasound probe 107 during the short axis approach. Once the needle 110 has been inserted into the skin 112, the Hybrid Guide 100 is disengaged from the short axis notch and rotated 90° clockwise 118 (FIG. 5) without disengaging the transducer probe 107/109/108.

Figure 1A:
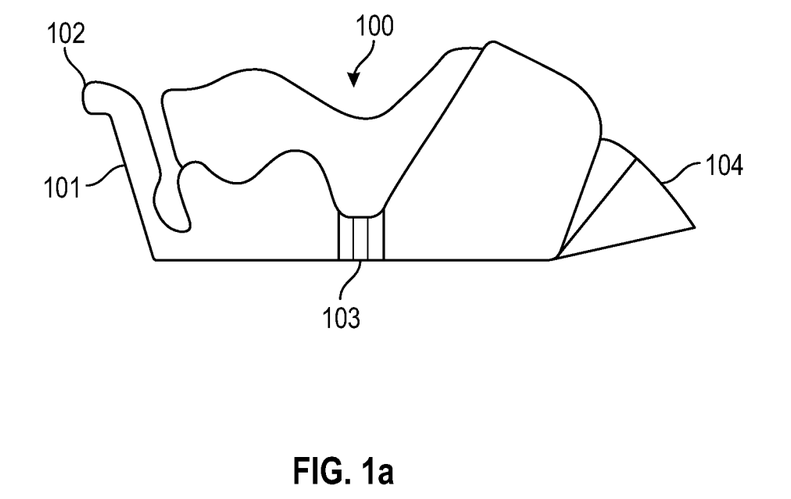
FIGS. 1a and 1b are side views of the Hybrid Guide.
Figure 1B:
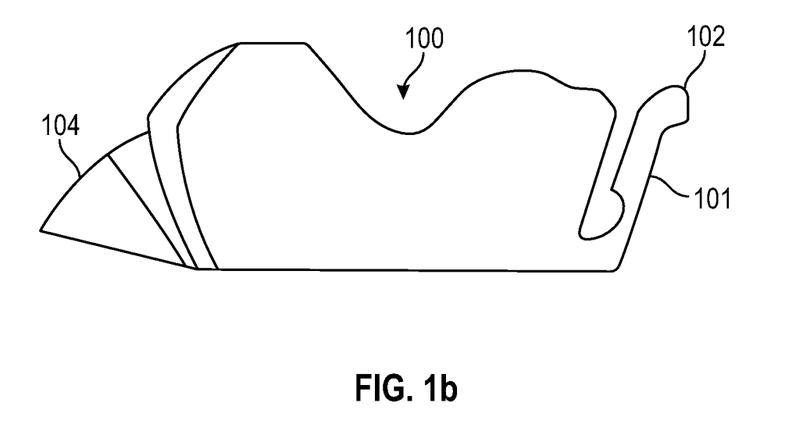
Figure 1C:
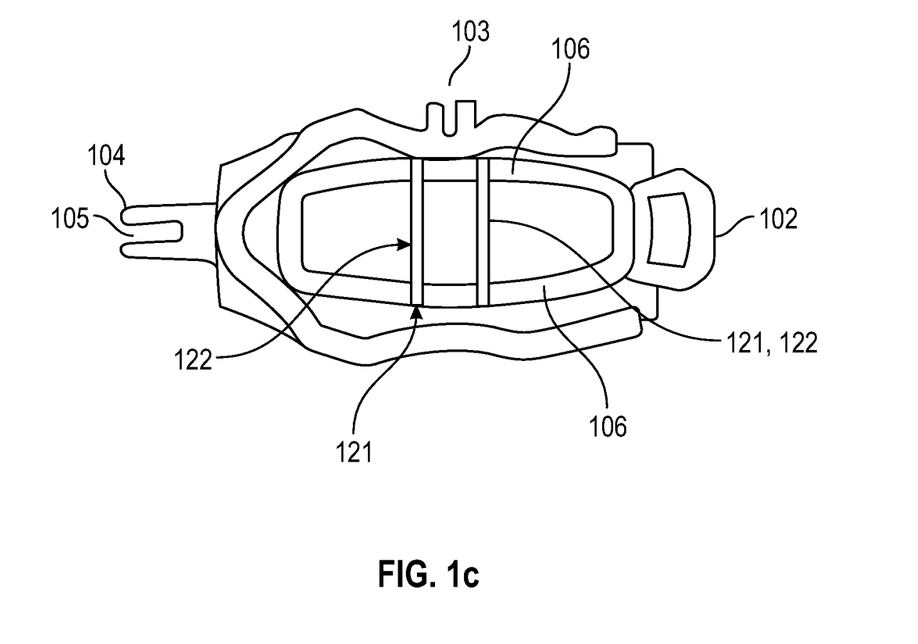
FIG. 1c is a top view of the Hybrid Guide of FIGS. 1a and 1b.
Figure 1D:
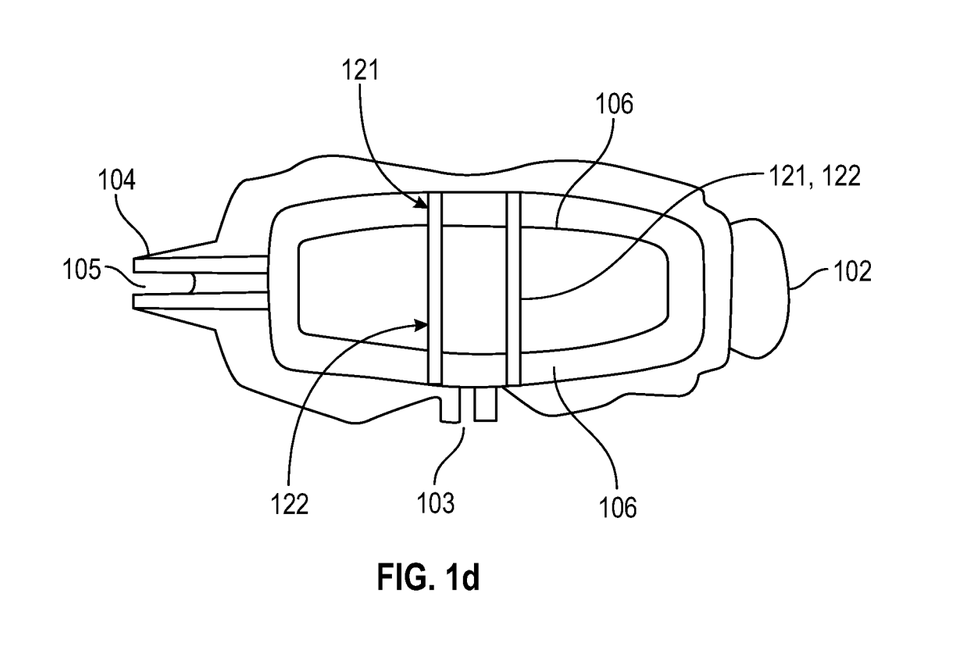
FIG. 1d is a bottom view of the Hybrid Guide of FIGS. 1a and 1b.
Figure 1E:
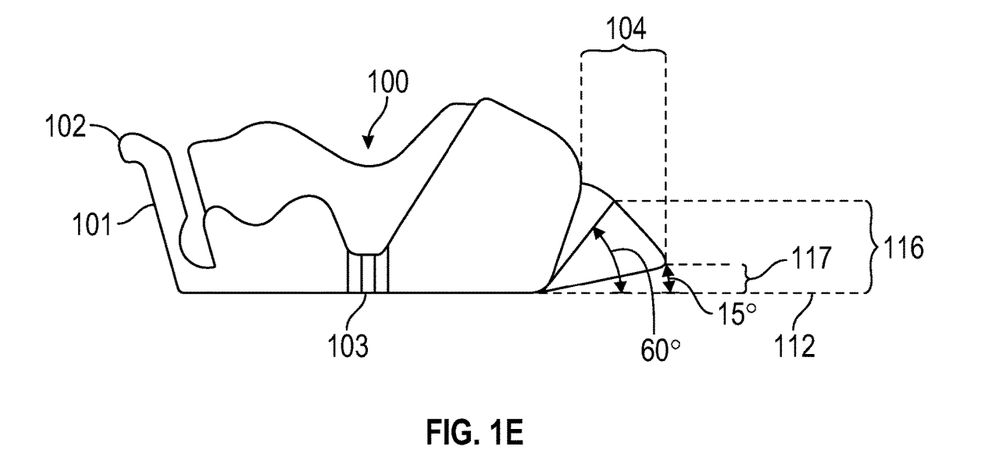
FIGS. 1e and 1f are side views of the Hybrid Guide showing the angle of the needle slot.
Figure 1F:
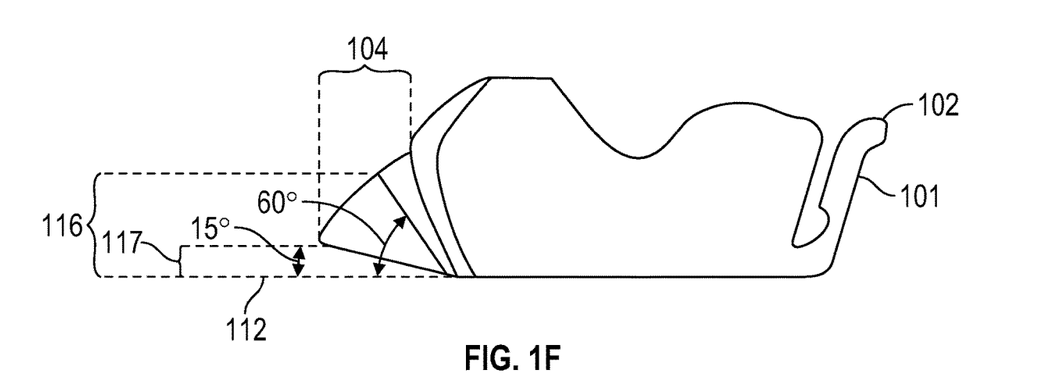

Hybrid Guide 100 preferably includes a needle guide 104 termed the "long axis needle guide" 104. The long axis needle guide has a slot 105 that the needle shaft 110 is placed into. The needle 110 is now enclosed within the long axis needle guide 104 and held in the long axis of the ultrasound beam. In a presently preferred embodiment, the long axis needle guide slot 105 of the Hybrid Guide 100 has a maximum angle that can range from 60° to 30° (depending on the type of Hybrid Guide used) from the planar bottom surface XX of Hybrid Guide or skin 112, 116 (FIGS. 1E, 1F). However, the invention is not limited to a 60 degree angle, and other suitable angles may be used. When the needle 110 is in the skin 112 and the Hybrid Guide long axis needle guide 104 is overlying the needle shaft 110, the clinician places the shaft of the needle 110 at the 60° block angle 116 of the long axis needle guide 104 and slightly braces the needle shaft 110 against the body of the long axis guide 104 along the 60° block angle 116. This serves to stabilize the needle 110 in the long axis direction at a 60° angle, while holding it in the ultrasound beam. Also, the point of contact of the needle shaft 110, the skin 112, and the base of the Hybrid Guide 100 on the transducer 109 forms a second stabilizing point. The needle 110 is completely stabilized in all directions. The needle 110 is now aligned in the long axis ultrasound beam, which is aligned with the long axis of the vessel 113. The needle 110 is stabilized in this position, while being advanced into the vessel 113. The clinician will see the entirety of the needle shaft 110 during this procedure. At this point, the needle 110 can be used to puncture the vein 113, followed by guidewire 115 advancement. Alternatively, the needle 110 can be lowered (advanced) toward the skin 112, for a lower angle allowing easier puncture of the vessel 113. According to a presently preferred embodiment, the Hybrid Guide 100 has a 15° release angle 117 (FIGS. 1e, 1f) from the skin 112 (bottom surface of the Hybrid Guide). The release angle provides clearance between the skin and the bottom surface of the Hybrid Guide 100 designed to allow the clinician to advance a catheter over needle 110, if that technique is being used. However, the invention is not limited to a 15 degree release angle, and other suitable angles may be used. The catheter can then slide under the Hybrid Guide 100 into the vessel 113 without lifting the ultrasound transducer probe 108, preventing loss of visualization during the procedure.

Hybrid Guide 100 designed to facilitate easy disengagement from the needle 110 by simply sliding it off the needle shaft 110. The practitioner then can complete the intravenous access procedure.

The Device

The Hybrid Guide 100 is designed to precisely fit the transducer 107/108/109.

Figure 2A:
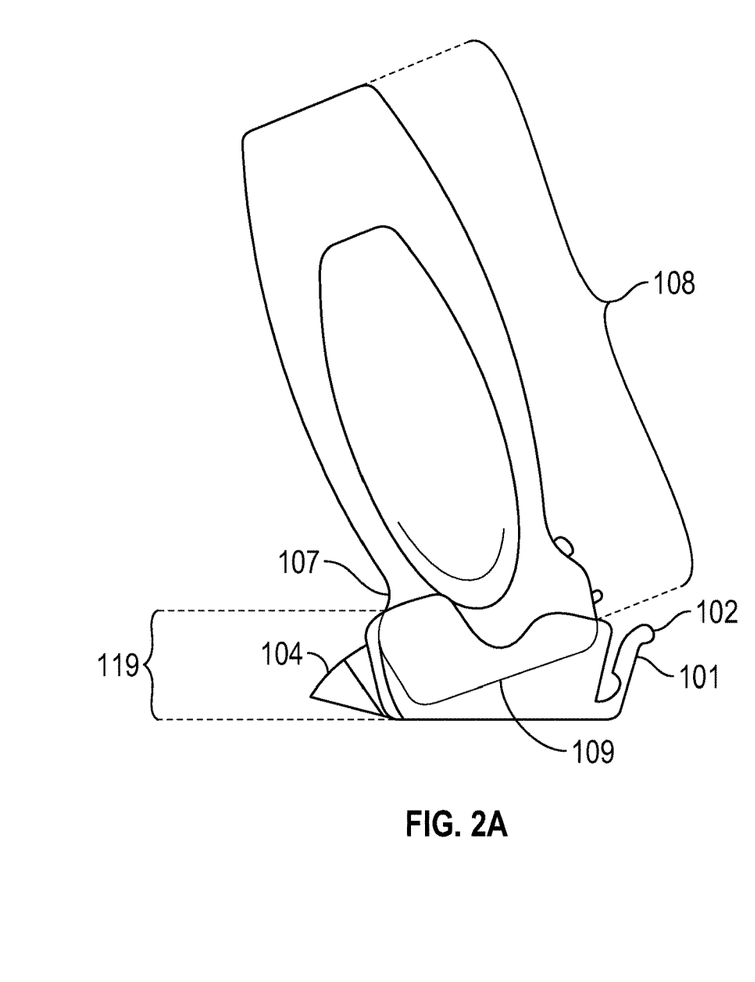
FIGS. 2a and 2b are side views showing the transducer inserted into the Hybrid Guide.
Figure 2B:
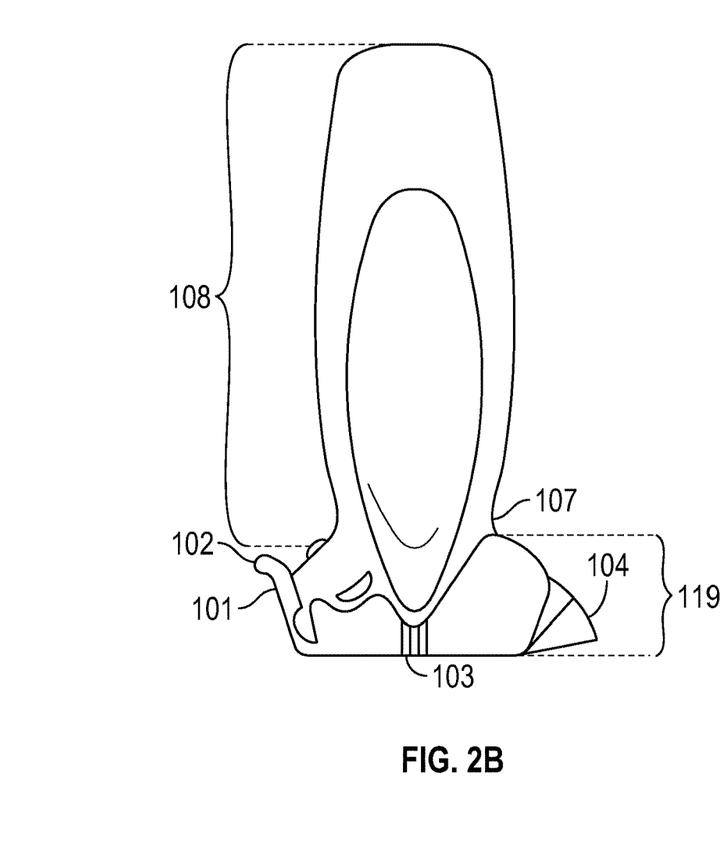

1. The long axis end of the Hybrid Guide 119 (FIG. 2) acts as a cup (receptacle) for insertion of the long axis guide end of the ultrasound transducer 107, (FIG. 2). This forms a snug custom fit of the Hybrid Guide to the transducer head and secures the long axis guide into centering alignment with the ultrasound beam.

2. Tensioning Clip 101/102 applies constant pressure pressing the ultrasound transducer into the cup of the long axis end of the Hybrid Guide.

3. Unibody Design with Support Fins 100: The Hybrid Guide 100 is preferably a single-piece (unibody) unit giving it rigidity in all directions. However, the device may be broken into two or more component parts as needed to facilitate manufacturing. The illustrated embodiment preferably includes two or more support fins 106 provided within the cup-like receptacle and which circumscribe the base of the guide 107/109. Support Fins 106 grip the transducer face 109 without interfering with the ultrasound beam. According to a preferred embodiment fins 106 are 1 mm wide; however, other dimensions are also possible and fall within the scope of the invention. The combination of the support fins 106 and unibody design make a very stable attachment and predictable needle 110 alignment.

4. Long Axis Guide 400: The Hybrid Guide 100 preferably includes a long axis guide 104 on the short end of the transducer probe. The long axis guide 104 is preferably on the end of the probe that correlates to the appropriate alignment on the ultrasound screen for standard orientation of venous cannulation for the clinician. According to a presently preferred embodiment, the slot 105 in the long axis guide 104 is sized specifically for an 18-gauge needle for central line placement. One of ordinary skill in the art will appreciate that the long axis guide 104 may be sized for any desired gauge needle. According to a presently preferred embodiment, the needle is supported at a 60° angle in the long axis. This is designed to add additional stabilization at the appropriate entry angle for central line placement. According to a presently preferred embodiment, the guide terminates 15° 117 from the surface of the skin 112 when the transducer with the guide 109/100 is applied to the skin surface 112. However, the invention is not limited to any particular angle and other angles may be implemented. This is designed to allow the clinician to advance the needle 110 and or catheter underneath the guide 104 into the vessel 113 while simultaneously maintaining continuous visualization of the procedure via ultrasound screen, therefore having complete visualization (FIG. 9) of the entirety of the procedure to completion.

5. Short Axis Notch 300: Hybrid Guide 100 preferably includes a short axis notch 103 configured to facilitate centering the needle in the midpoint of the ultrasound beam in the short axis view.

6. Clip and Release 101/102: The presently preferred embodiment of the Hybrid Guide 100 includes a unique tensioning clip 101/102 design. The tensioning clip 101/102 is ergonomically designed to be held and actually assist the clinician's grip on the transducer 108 during the procedure. The transducer probe head 109 snaps into the Hybrid Guide 100, allowing the clip 101/102 to hold the transducer head 109 firmly in place and in alignment. Releasing the transducer head is simple: pull the tab 102 to release the Hybrid Guide 100 from the transducer 108. The Hybrid Guide may include any release mechanism and is not limited to the specific embodiment illustrated in the drawings.

7. Targeting Bands: The Hybrid Guide 100 may optionally include targeting bands 122 formed of an echogenic material visible under ultrasound visualization. The targeting bands 122 aligned across the center of the transducer face 109. They traverse the ultrasound beam. The two targeting bands 122 are placed equidistant from the centerline of the transducer. They may, for example, be composed of non-latex rubber. The targeting bands 122 form an interference pattern 123 (FIG. 4) on the ultrasound image screen (FIG. 4) that appears in a star-like formation. Since the targeting bands 122 are affixed to the Hybrid Guide-transducer unit (FIG. 2), they appear to move across the ultrasound screen (FIG. 4) as a unit when the clinician moves the transducer 108 across the surface of the skin to localize the vessel 113. This allows the clinician to approximate the center of the vessel 113 in short axis more accurately and with very minimal effort.

8. Targeting Band Slot: The Hybrid Guide 100 may optionally include targeting band slots 121 for receiving the Targeting Bands 122. The Targeting Bands, if provided, may optionally be molded into the Hybrid Guide 100 thereby eliminating the need for targeting band slots 121. According to a presently preferred embodiment, targeting band slots 121 are provided in the cuplike receptacle of the Hybrid Guide 100 proximate the transducer grip fins 131 (FIGS. 1E, 1F). The targeting band slots 121 are configured to accept the targeting band 122. The targeting bands 122 are flush to the ultrasound transducer probe face 109 of the Hybrid Guide 100 on the skin.

The Procedure:

1. The Hybrid Guide 100 is designed to use with sterile technique. The Hybrid Guide 100 is placed on a flat surface or held in the palm of the gloved hand. If using sterile technique, a sterile vinyl ultrasound sleeve is placed on the transducer head. The Hybrid Guide 100 itself is sterile in the packaging. The smooth end of the ultrasound transducer probe 107, which has no elevated tabs or alignment features, is inserted into the Hybrid Guide 100 at a 45° angle.

2. When the Hybrid Guide 100 end of the transducer probe 107 is inserted into the Hybrid Guide 100/200, it is pushed down on the snap release mechanism 101/102 and locks in place 200. The Hybrid Guide 100 is now firmly attached to the transducer probe 107/109/108 and ready for use.

3. Ultrasound gel is applied to the area of the patient where IV cannulation is desired. The short axis approach 300 is used to visualize the vessels in a transverse plane. The probe is compressed into the patient's flesh. The vein 113 will readily compress relative to the artery, allowing the clinician to identify the appropriate vein 113 for cannulation. The transducer probe 108 is then held in the transverse plane and moved up and down the long axis of the vein 113 to confirm linearity. This rules out tortuosity of the vein. The vessel 113 is now centered between the targeting band interference patterns 123 on the ultrasound screen (FIG. 4) by moving the ultrasound transducer probe 108 back and forth in the transverse direction. The transducer probe 108 is now in position for puncture of the skin 112.

Figure 3:
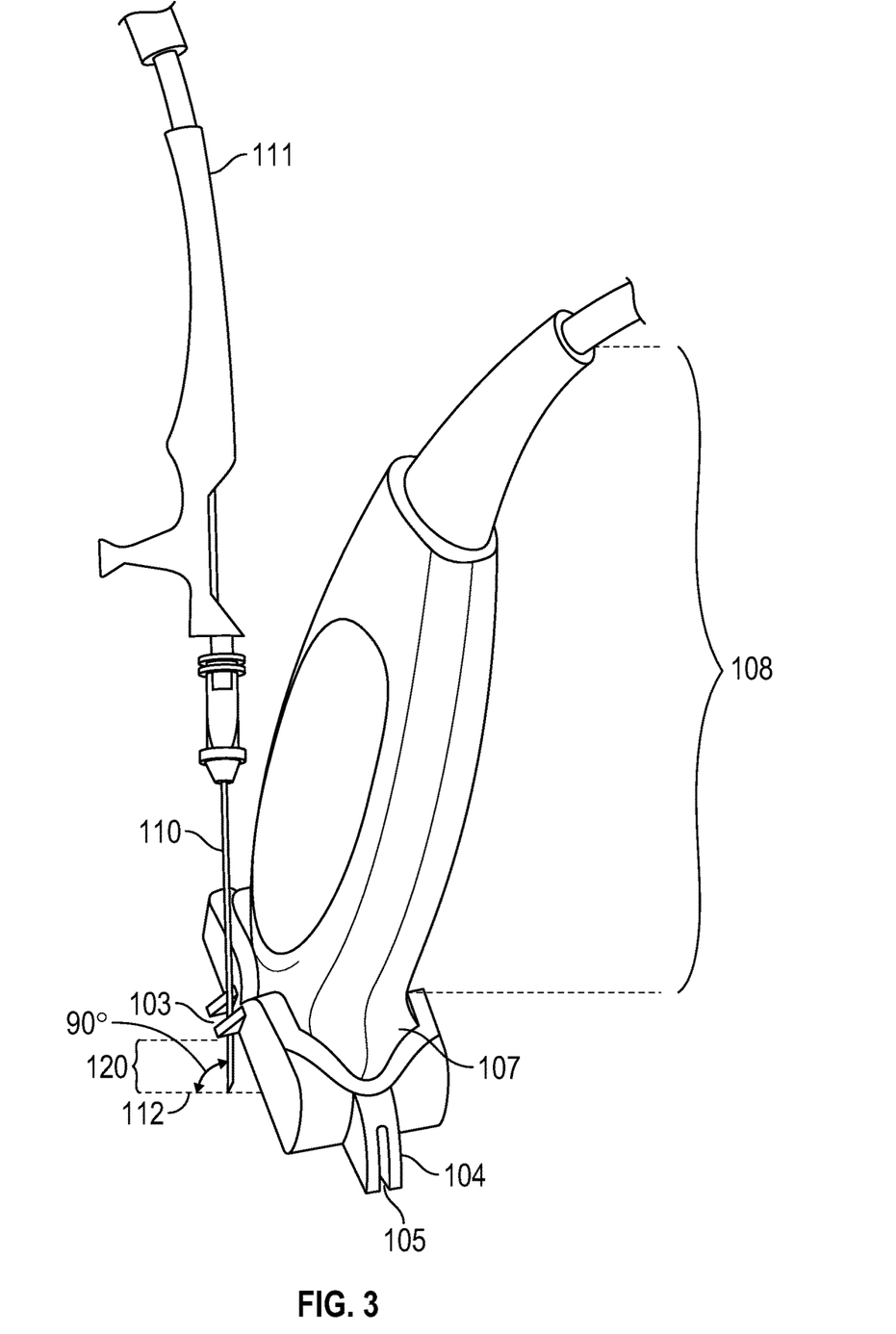
FIG. 3 is a perspective view of the Hybrid Guide in the Short Axis orientation with WinGuide 111.
Figure 4:
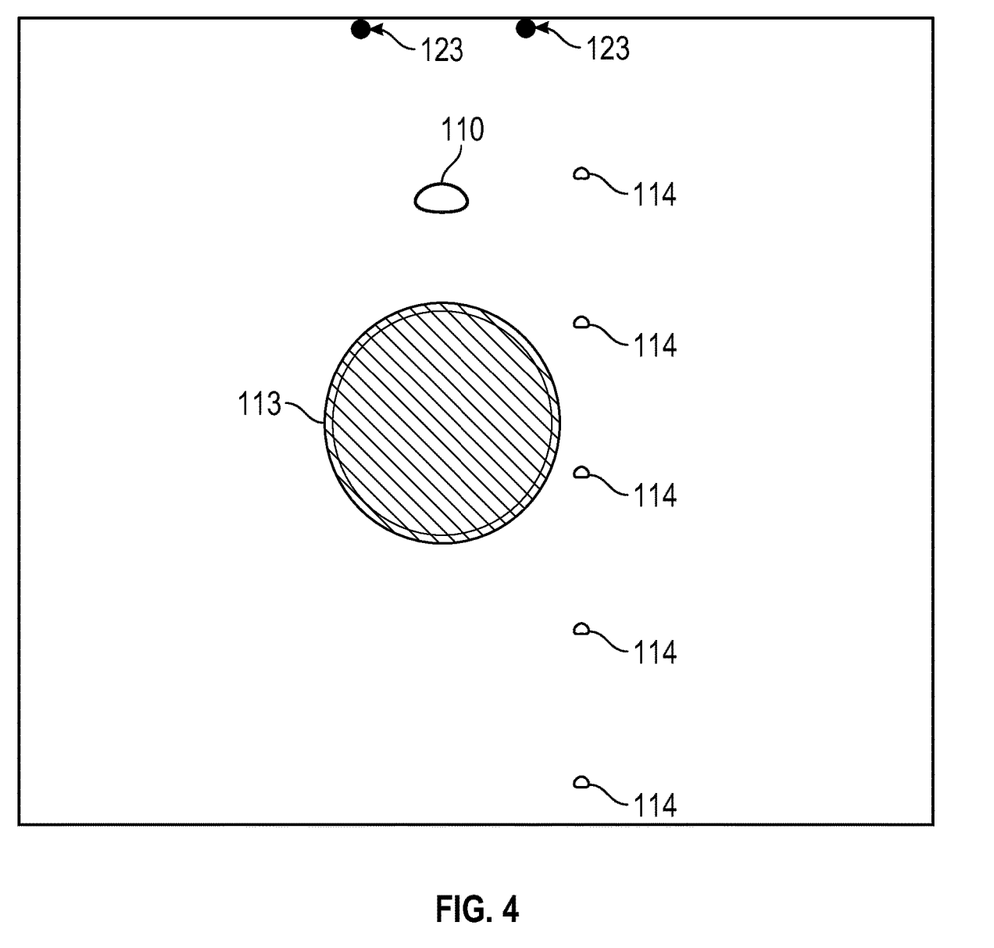
FIG. 4 is a simulation of an ultrasound visualization in the short axis orientation.

4. The clinician centers the cross-section of the vein 113 into the center of the ultrasound screen. The center of the ultrasound screen correlates to the short axis notch 103 in the Hybrid Guide 100. The clinician now inserts the needle 110 at approximately 60° to 90° angle 120 (FIG. 3) to puncture the skin 112 only (FIG. 4).

Figure 5:
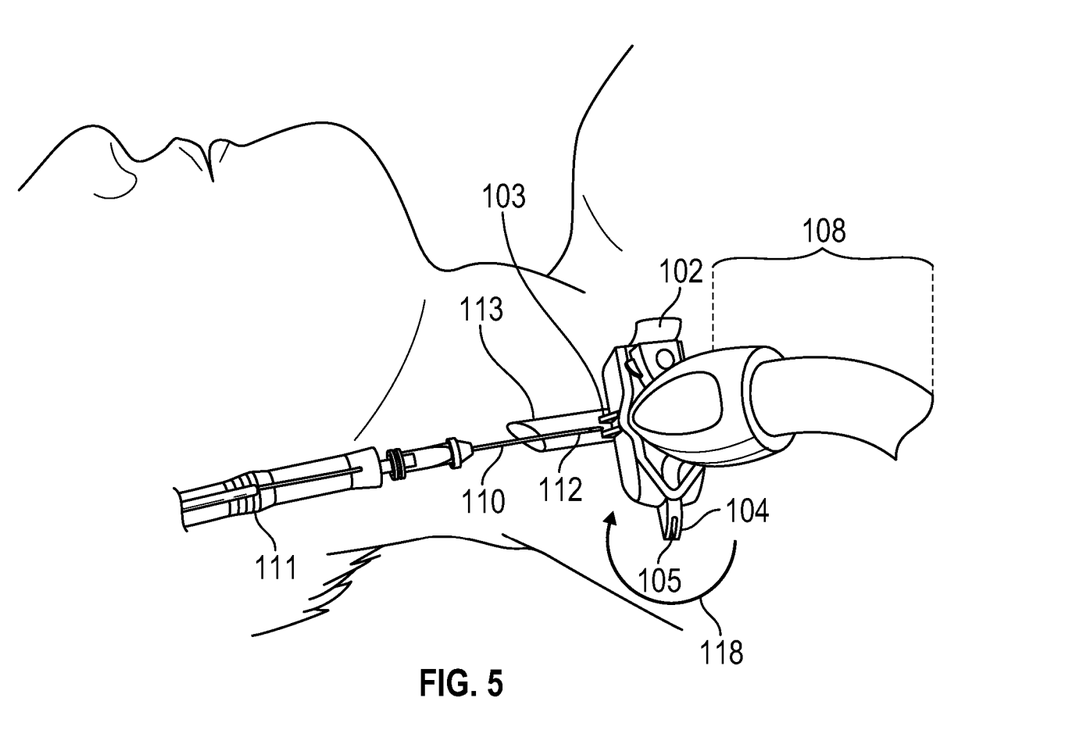
FIG. 5 is a perspective view of the Hybrid Guide in the Short Axis orientation with WinGuide 111.

5. Once the skin 112 is punctured, the ultrasound probe 108 is removed from the needle 110 and the skin 112 insertion site. The ultrasound probe 108 with Hybrid Guide 100 attached is rotated counterclockwise 90° 118 (FIG. 5).

Figure 6:
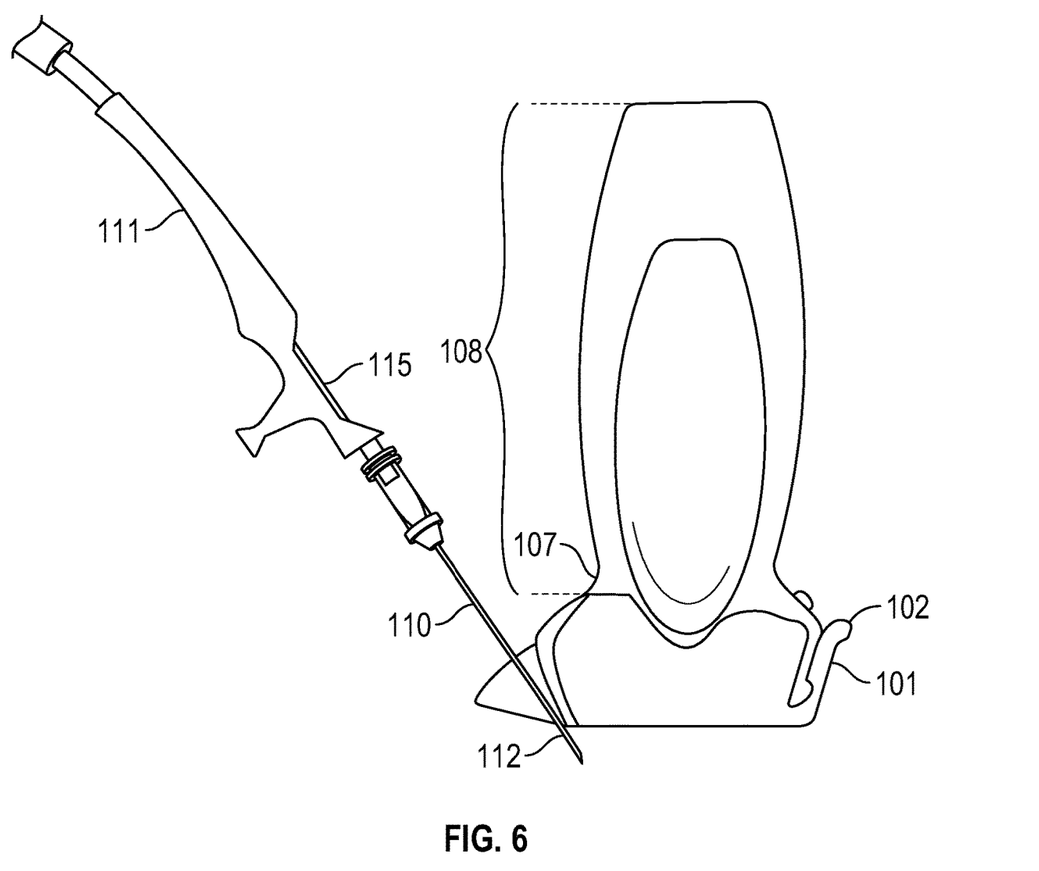
FIGS. 6 and 7 are perspective views of the Hybrid Guide in the Long Axis orientation with WinGuide 111.
Figure 7:
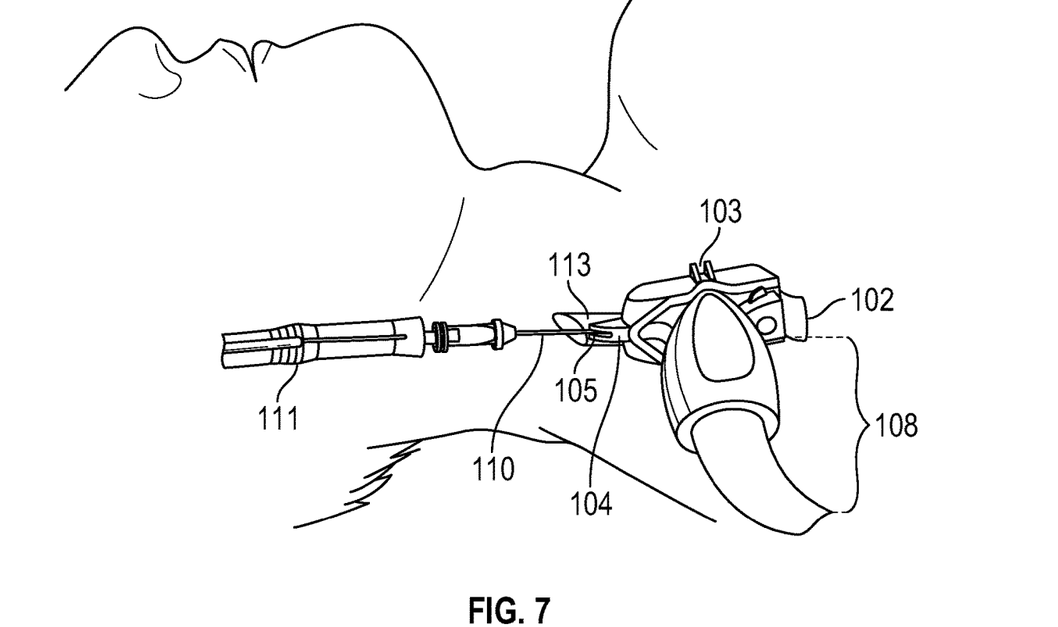
Figure 8:
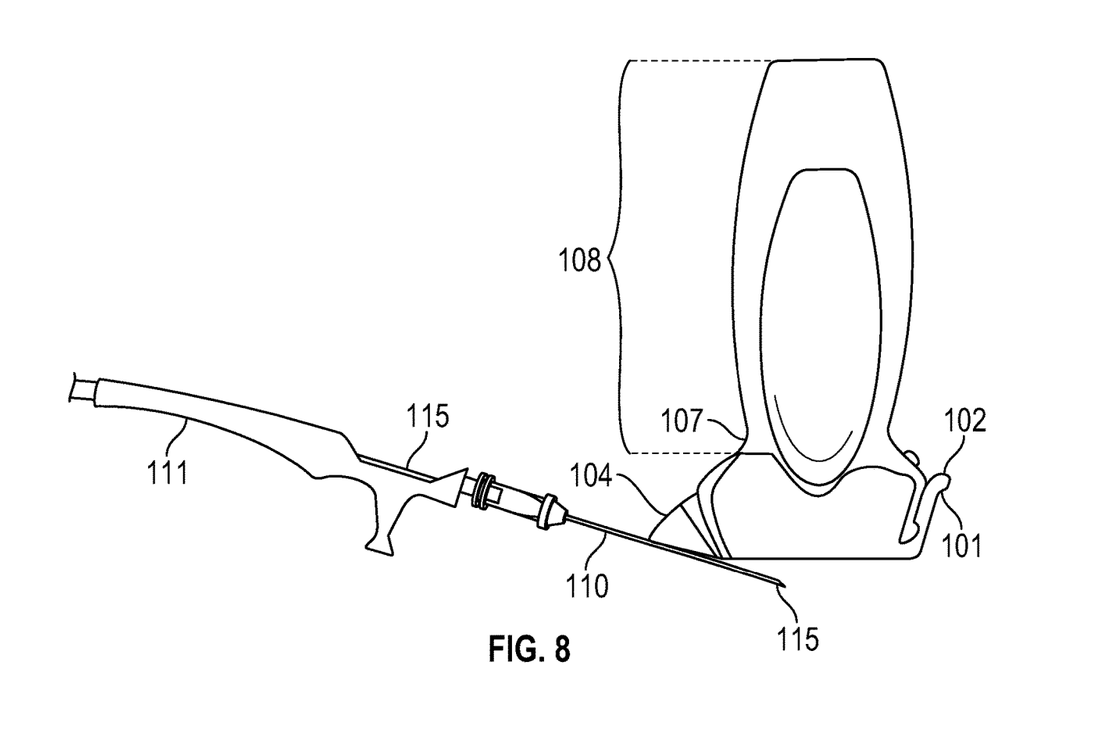
FIG. 8 is a side view of the Hybrid Guide in the Long Axis orientation with WinGuide 111.
Figure 9:
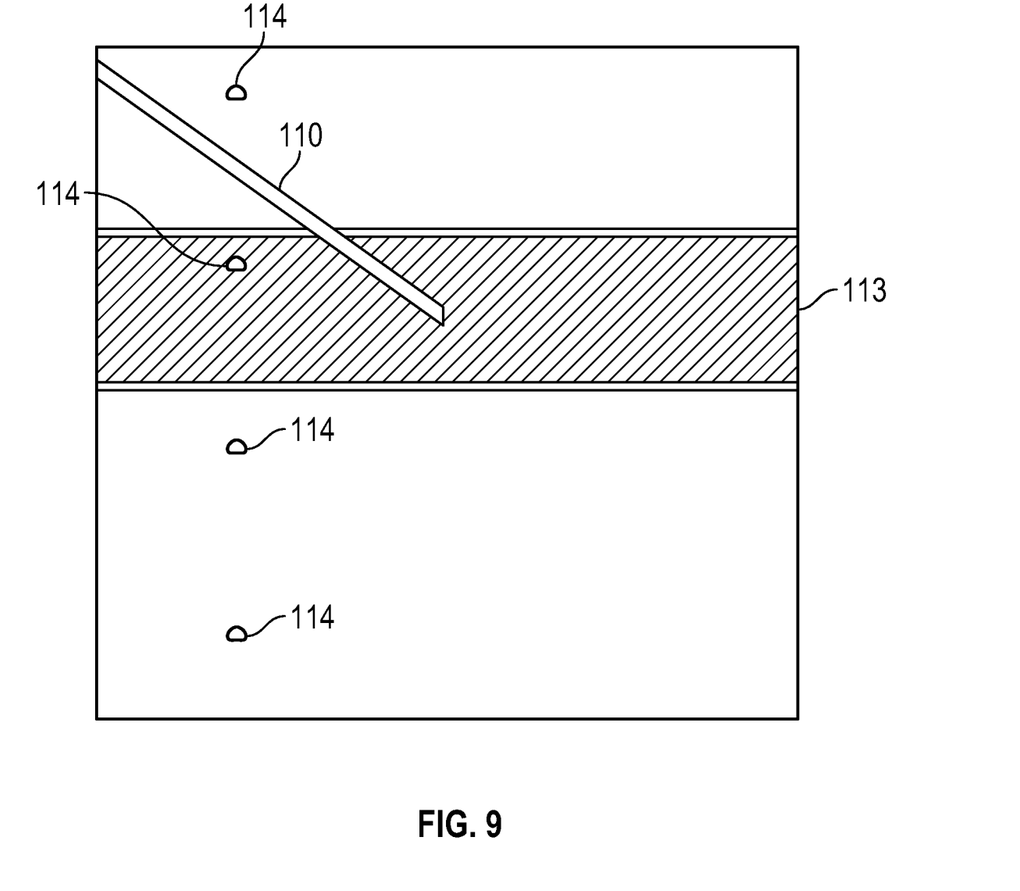
FIG. 9 is a simulation of an ultrasound visualization in the Long Axis orientation.

6. The ultrasound probe 108 is rotated so that the long axis guide 104 can be set onto the needle 110 that is inserted into the skin 112 (FIG. 6), 400. The long axis guide 104 is slightly pressed against the base of the needle 110 with the needle 110 shaft slightly pressing against the 60° base of the long axis needle guide slot 105 of the Hybrid Guide 100. This completely stabilizes the needle 110. The ultrasound transducer head 109 is rotated over the long axis of the vein 113, pivoting upon the needle 110 insertion point in the skin 112 to obtain a centered long axis view of the vessel to be cannulated. Once the long axis of the vein 113 is centered, the needle 110 is advanced with complete stability. The clinician watches the needle 110 advance into the vein 113 on the ultrasound video screen (FIG. 9). At times the needle 110 won't puncture the vein 113, particularly when a patient is in a hypovolemic state. If this situation occurs, the needle 110 can be dropped toward the skin surface to a lower angle approach that applies more traction on the wall of the vein 113, thereby puncturing the vein 113. In either case, the needle 110 will enter into the vein 113. Using the WINguide 111, the guidewire 115 is immediately advanced into the vein 113, securing placement.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A positioning fixture for use with an ultrasound transducer comprising:
    a base having a planar bottom surface and top surface, each of the planar bottom surface and the top surface having two long edges and two short edges, the top surface facing away from the bottom surface;
    first and second echogenic targeting bands recessed below the bottom surface of the housing, each of said first and second echogenic targeting bands extending between said two long edges of the base, across a face of the ultrasound transducer, such that said first and second echogenic targeting bands form an interference pattern visible under ultrasound visualization, wherein the interference pattern is used to locate the positioning fixture relative to structures visible under ultrasound visualization;
    a pair of long sidewalls provided on and extending orthogonally from the top surface, one long sidewall of the pair of long sidewalls is attached to each of said two long edges;
    a guide release on the top surface, attached to one of said two short edges on the top surface;
    a long axis needle guide on the top surface, attached to another of said two short edges; and
    a receptacle cooperatively defined by said pair of long sidewalls, said guide release and said long axis needle guide, said receptacle sized to accommodate the ultrasound transducer.

2. The positioning fixture of claim 1, further comprising a short axis notch provided on at least one of the pair of long sidewalls, said short axis notch sized and configured to accept a needle.

3. The positioning fixture of claim 1, wherein the long axis needle guide includes a long axis notch sized and configured to accept a needle.

4. The positioning fixture of claim 2, wherein the first echogenic targeting band is positioned proximally of the short axis notch and the second echogenic targeting band is positioned distally of the short axis notch.

5. The positioning fixture of claim 1, further comprising two or more support fins provided within the receptacle, said support fins extending orthogonally from the top surface and configured to support and grip the transducer.

6. The positioning fixture of claim 1, wherein an angular orientation of the long axis needle guide is adjustable.

7. The positioning fixture of claim 1, wherein the long axis needle guide includes at least two long axis notches provided at different angular orientations.

8. The positioning fixture of claim 1, wherein the long axis notch defines an angle ranging from 30 to 60 degrees relative to the bottom surface of the housing.

9. A method of inserting a needle into a patient's vein under ultrasound guidance, comprising:
    providing a hybrid guide including:
        a housing having a planar bottom surface and a top surface, each of the planar bottom surface and top surface having two long edges and two short edges, the top surface facing away from the bottom surface;
        first and second echogenic targeting bands provided on the bottom surface of the housing, each of said first and second echogenic targeting bands extending between said two long edges of the base, across a face of the ultrasound transducer such that said first and second echogenic targeting bands form an interference pattern visible under ultrasound visualization, wherein the interference pattern is used to locate the positioning fixture relative to structures visible under ultrasound visualization;
        a pair of long sidewalls provided on and extending orthogonally from the top surface, one said long sidewall of the pair of long sidewalls is attached to each of said two long edges;
        a short axis notch provided on at least one of the pair of long sidewalls, said short axis notch sized and configured to accept a needle;
        a guide release attached to one of said two short edges;
        a long axis needle guide attached to another of said two short edges, said long axis needle guide having a long axis notch; and
        a receptacle cooperatively defined by said pair of long sidewalls, said guide release and said long axis needle guide;
    inserting an ultrasound transducer into the receptacle; and
    adjusting a position of the housing under ultrasound visualization using the targeting bands such that the short axis notch is centered over the vein;
    inserting the needle into the short axis notch and piercing the subject's skin;
    disengaging the needle from the short axis notch by lifting the hybrid guide off of the needle, rotating the hybrid guide 90 degrees, and placing the needle into engagement with the long axis needle guide; and
    advancing the needle into the vein.

* * * * *